(12) United States Patent
Arco et al.

(10) Patent No.: US 7,875,012 B2
(45) Date of Patent: Jan. 25, 2011

(54) ELASTIC DISPOSAL MEANS

(75) Inventors: Judith A. Arco, Woodbury, MN (US); Leigh E. Wood, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 426 days.

(21) Appl. No.: 11/317,508

(22) Filed: Dec. 23, 2005

(65) Prior Publication Data

US 2007/0149942 A1    Jun. 28, 2007

(51) Int. Cl.
*A61F 13/15* (2006.01)
*A61F 13/20* (2006.01)

(52) U.S. Cl. .................. 604/385.13; 604/389
(58) Field of Classification Search ............ 604/385.13, 604/389
See application file for complete search history.

(56) References Cited

U.S. PATENT DOCUMENTS

| | | | |
|---|---|---|---|
| 3,676,242 A | | 7/1972 | Prentice |
| 4,772,282 A | | 9/1988 | Oakley |
| 4,963,140 A | | 10/1990 | Robertson et al. |
| 5,053,028 A | | 10/1991 | Zoia et al. |
| 5,071,414 A | | 12/1991 | Elliott |
| 5,575,784 A | * | 11/1996 | Ames-Ooten et al. .. 604/385.11 |
| 5,759,181 A | | 6/1998 | Sayama et al. |
| 5,773,374 A | | 6/1998 | Wood et al. |
| 5,807,371 A | | 9/1998 | Toyoda et al. |
| 5,853,881 A | | 12/1998 | Estey et al. |
| 5,910,225 A | | 6/1999 | McAmish et al. |
| 5,942,308 A | | 8/1999 | Arakawa et al. |
| 6,063,066 A | | 5/2000 | Inoue et al. |
| 6,264,644 B1 | | 7/2001 | Igaue et al. |
| 6,544,242 B1 | | 4/2003 | Kido et al. |
| 6,645,189 B2 | | 11/2003 | Kurita |
| 2002/0052593 A1 | | 5/2002 | Kurita et al. |
| 2003/0065302 A1 | * | 4/2003 | Kuroda et al. .......... 604/385.13 |
| 2004/0064123 A1 | | 4/2004 | Kawata et al. |
| 2005/0177127 A1 | * | 8/2005 | Ashton et al. ............... 604/391 |

FOREIGN PATENT DOCUMENTS

| | | |
|---|---|---|
| EP | 0 768 074 | 4/1997 |
| EP | 0 815 820 | 1/1998 |
| EP | 0 890 351 | 1/1999 |
| EP | 0 752 239 | 4/2000 |
| JP | 10-130592 | 10/1996 |
| JP | 11-192261 | 7/1999 |
| JP | 2001-95847 | 9/1999 |
| JP | 2001-137287 | 5/2001 |
| JP | 2001-137288 | 5/2001 |
| JP | 2001-137289 | 5/2001 |
| JP | 2002088322 | 3/2002 |
| WO | WO 00/37004 | 6/2000 |

* cited by examiner

*Primary Examiner*—Melanie J Hand
(74) *Attorney, Agent, or Firm*—Aleksander Medved

(57) ABSTRACT

There is provided an expandable disposal tape for use in a disposable absorbent article comprising an extensible base layer, the base layer having an attachable portion and an expandable portion. The expandable portion is formed of an extensible web material and further is provided with one or more lines of separation such that the expandable portion can be expanded to form at least one loop. This loop can then be extended by extending the extensible web material.

30 Claims, 5 Drawing Sheets

ELASTIC DISPOSAL MEANS

The present invention relates to disposable absorbent articles and specifically to an integral elastic element for securing a rolled or folded form of the article for compact disposal.

Disposable absorbent articles such as adult or baby diapers and feminine hygiene articles are conventionally rolled up and disposed of following use. This is an intuitive process by the user. The soiled side is rolled or folded onto itself by the user. The problem is how to keep this rolled or folded shape during the generally short time period prior to disposal. Tape tabs or fastening tabs of some sort have been the traditional approach. These could be, in the case of diapers at least, the fastening tabs which were used to keep the diaper on the wearer, as discussed for example in U.S. Pat. Nos. 5,759,181; 4,963,140 and 5,053,028.

The problem with this approach is that these fasteners could be contaminated, particularly, if they are adhesive, or there may not be a suitable surface to which the fastener can adhere. When adhesive or mechanical fasteners are used, generally an engineered surface is provided to which the fastener can adhere. This is a suitable loop for a hook type mechanical fastener, or a frontal landing surface for an adhesive fastener. However, these engineered surfaces are expensive and as such are not placed over the entire diaper outer surface and therefore are often not available for use when the diaper is folded unless the user is instructed to fold or roll the diaper in a very specific way. As most users are not likely to roll or fold the diaper the same way even if provided with instruction on the package, finding or providing suitable surfaces to attach fasteners can be problematic. It is nearly impossible to educate all users to dispose of the product in only one specific manner.

Other approaches have tried to avoid the use of tapes or other fasteners and provide disposable elements that were perhaps more intuitively apparent to the end user. U.S. Pat. No. 5,071,414 proposes a pocket provided in a diaper. This however is something that may be missed by most users and is difficult feature to add with a conventional high-speed diaper line.

U.S. Pat. Nos. 5,942,308, 6,063,066, and 6,544,242 propose disposal tapes provided at a separate location of the disposable article just for use in disposability. A disposal tape can be placed at a location where it is more likely to be available for use after the disposable article is rolled or folded for disposal. This is generally the back outside surface of a diaper. However, the user still must have a suitable surface on to which to adhere the adhesive fastener. This could be a random location selected by the user. As such this approach suffers from some of the same problems as using the primary fastener for disposal.

Other approaches to modify the diaper design include U.S. Patent Publication 2002/0052593 which has slots built into the side edges of a pull-on type diaper and U.S. Patent Publication 2004/0064123 which provides a diaper with large straps to be used by the user for disposal. These approaches add significant complexity to diaper manufacturing, are not necessarily intuitive in their use and, with the latter, has the issue of large straps hanging off the diaper which would likely be used by a baby to remove the diaper, or otherwise use inappropriately.

The present invention is directed at providing a disposal element on an absorbent article which is easily incorporated by the manufacturer of the article, is intuitive for the end user and is not dependent on providing a suitable attachment surface for the end user to find.

SUMMARY OF THE INVENTION

The invention is directed at an expandable disposal tape for use in a disposable absorbent article comprising an extensible base layer, the base layer having an attachable portion and an expandable portion. The expandable portion is formed of an extensible web material and further is provided with one or more lines of separation such that the expandable portion can be expanded to form at least one loop. This loop can then be extended by extending the extensible web material.

DETAILED DESCRIPTION OF PREFERRED EMBODIMENTS

Figure 1A:
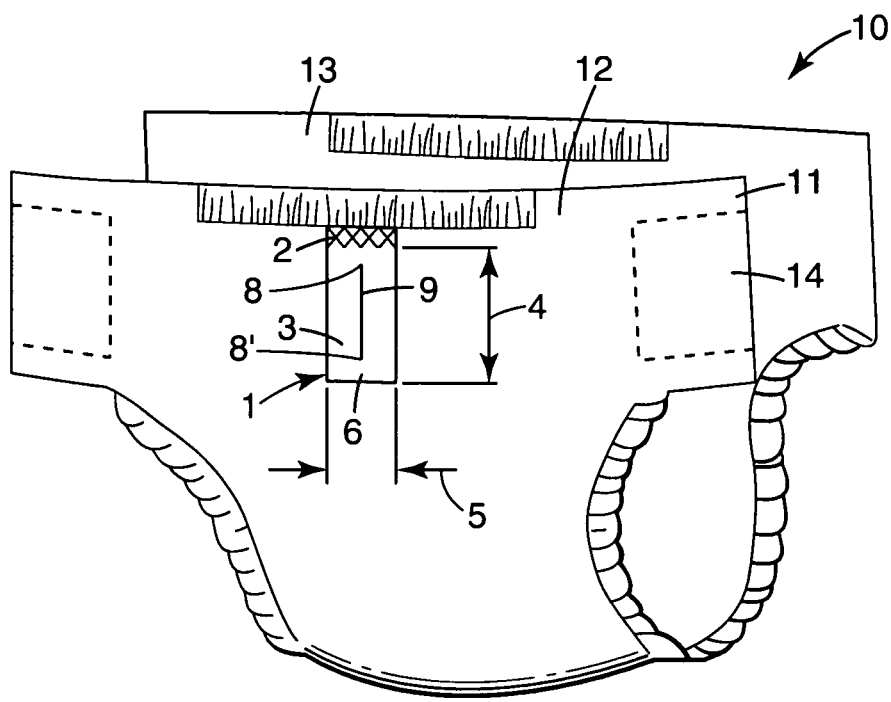
FIGS. 1a and 1b are perspective views of a disposable diaper using an expandable disposal tape of the invention.

The invention expandable disposal tape is designed for use in conventional disposable articles such as adult or baby diapers or incontinent products, feminine hygiene products, surgical gowns, absorbent pads, pet absorbent items or the like. By tape it is meant a strip of material which may or may not have adhesive coated on a face of the strip of material. Generally the invention is used with disposable articles that are, or can be, soiled and are, or can be, conventionally rolled up by the user prior to disposal. An example of a conventional disposable article that is rolled up for disposal is an adult brief or baby diaper 10 as shown in FIG. 1a. The disposable diaper 10 has a body facing surface 13 and a back surface 12 facing away from the wearer. On the side edges 11 are provided fastening surfaces 14 that keep the diaper closed around the wearer when in use. These fastening surfaces 14 would conventionally be adhesive or mechanical type fasteners and could be part of the diaper as shown or more commonly provided on separate tab elements.

The invention expandable disposal tape 1 is provided on the back surface 12 of the diaper 10 so that when the diaper 10 is rolled or folded up for disposal the invention disposal tape 1 is available for use. This could be any suitable surface on the back of the diaper 10, which has a high likelihood of being exposed when a typical consumer folds or rolls the soiled diaper 10 up for disposal. This could be a back surface near the edge of the diaper 10 as shown in FIG. 1a, or other locations such as near the crotch. The invention expandable disposal tape 1, as shown in the FIG. 1a embodiment, comprises a discrete extensible base material 3. The extensible base material 3 has an attachable portion 2, which is attached to the disposable article. This could just be the extensible base material 3 itself, which could be attached by adhesives, heat, ultrasonic bonding, pressure bonding or any other well known bonding means. In this case the material forming the base layer, on the side facing the back surface 12 of the disposable article, should be a material which is suitable for the selected bonding method. If heat or ultrasonic bonding to the back surface 12 of the disposable article is intended to be used, the base material should be heat or sonically bondable. This could be, for example, a thermoplastic film or thermoplastic fibrous layer or material. The attachable portion 2 could also be provided by a separate film or layer which could be suitable for thermal type bonding (e.g. ultrasonics or heat) or adhesive bonding or the like. This could be a surface receptive to thermal bonding or adhesive bonding. For adhesive bonding, it could also be the adhesive layer itself, such as a hot melt or pressure sensitive adhesive layer. It is also possible that the attachable portion 2 be releasably attachable to the disposable article by use of a breakable bond (e.g. light heat or ultrasonic bonding or light adhesive bonding) or use of a refastenable fastener such as a pressure sensitive adhesive or mechanical fastener (such as a hook material). With a refastenable hook material, the back of the disposable article must have a suitable fibrous loop type material to which the hook can attach. This could in some cases be a nonwoven used to form the back surface of the disposable article. The nonattached end of the disposal tape could also be lightly bonded to the disposable article to prevent flagging prior to use. This bond should be readily breakable or releasable. Alternatively the entire disposal tape could be lightly bonded to allow for removal.

The disposal tape also has an expandable portion having a length 4 formed from the extensible base material 3. The extensible base material 3 is formed of extensible web materials which could be a single layer web, such as a film or fibrous web, or a multilayer web having film, fibrous or other layers. By extensible web material or extensible base material it is generally meant a material that can easily be plastically or elastically deformed under light tension as might be used by an end user. This is generally a material that can deform by at least 50 percent, 100 percent or even 200 percent under tensions of less than 20 or 25 Newtons or preferably 15 Newtons or less.

The extensible base material is preferably an elastically extensible material. Elastic materials are preferred in that the retractive force of the elastic materials helps keep the article contained in its folded form for disposal. Inelastic materials could be used as they still can be wrapped around the folded or rolled article to aid in disposal. If the extensible material is particularly easy to extend, it could be preferred to provide a nonextensible reinforcing film or layer in the region of the attached portion 2 to prevent it from extending along with the expandable portion if this is not desired.

The expandable portion has a length 4 and a width 5, which is provided with one or more lines of separation 9. The line or lines of separation 9 allow the expandable portion to be opened to form at least one loop, which loop can grow in size, with extension of the extensible material. This loop is extended to a size such that it can accommodate wrapping around at least a portion of the disposable article The at least one line of separation 9 extends along either the length 4 and/or width 5 of the disposal tape expandable portion to provide at least two terminal ends 8, 8', and at least two bridging web portions 6, 6'. A line of separation 9 is preferably substantially parallel with at least one side edge 16 or 17 of the disposal tape. This generally maximizes utilization of the disposal tape so as to allow it to form a loop, which can be easily and uniformly expanded at a given tension. The line 9 of course could be straight or curved as a matter of design choice. The terminal ends 8, 8' of the lines of separation 9 terminate prior to reaching a side edge or another line of separation 9, creating the bridging web portions 6, 6'. These bridging portions 6, 6' allow the disposal tape 1 to form at least one loop without easily tearing. Generally these bridging portions will be from 1 to 50 mm or 2 to 30 mm from the terminal end 8, 8' to the side edges or another line of separation 9. Smaller widths are possible with stronger webs, or webs provided with reinforcing elements or webs in at least the bridging portion, particularly reinforcement at or adjacent the terminal ends 8, 8' of the lines of separation 9. When there are two or more lines of separation 9, some of the terminal ends 8, 8' can extend to a side edge of the disposal tape, or to another line of separation 9' of the disposal tape, creating a separable end 7. A separable end 7 does not form a bridging web portion 6, but rather it functions to divide the disposal tape into two separable halves each of which can form a separate loop or enlarge a single loop.

Figure 2A:
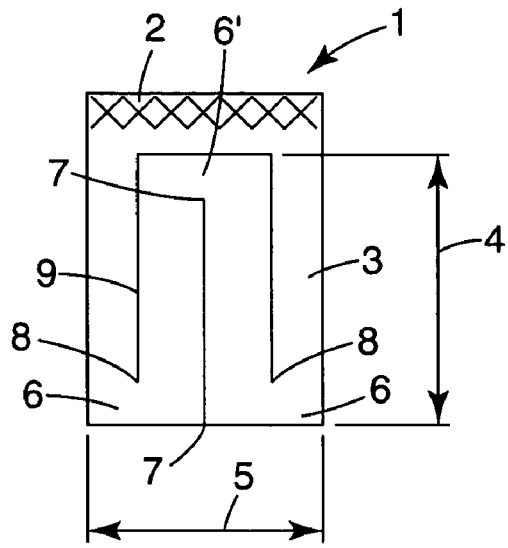
FIGS. 2a and 2b are plan views of an expandable disposal tape of the present invention.
Figure 2B:
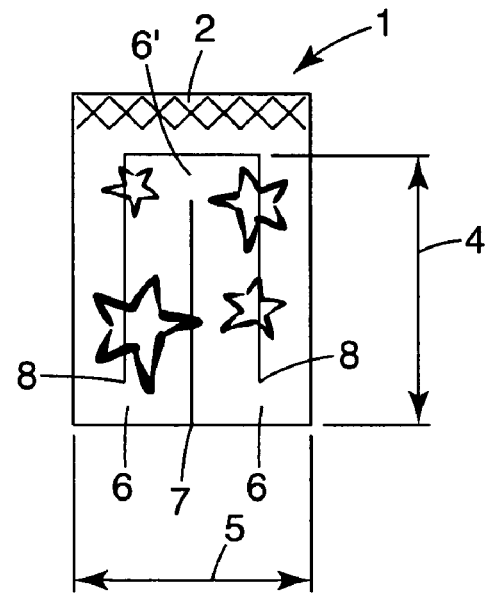
Figure 3:
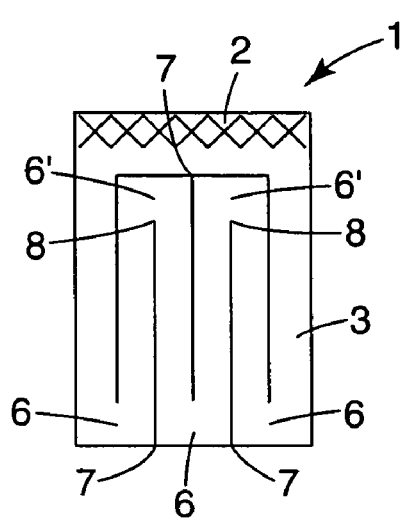
FIG. 3 is a plan view of another embodiment of an expandable disposal tape of the present invention.

This separable end 7 can allow the disposal tape 1 to be expanded into a larger loop prior to extending the extensive base material 3 as is shown in FIGS. 2a and 2b. This is possible if the bridging portion 6' formed by the terminal end 8' opposite a separable end 7 can be separated from the attached portion 2. This can occur, for example, where there is a line of separation 9 interposed between a terminal end 8' and a side edge 16 or 17 of the disposal tape and wherein a separable end 7 of the line of separation 9' is located at the side edge 17. This creates a separable bridging portion 6'. The separable end 7 in the embodiment of FIGS. 2a and 2b allows the formation of three (3) bridging portions (6, 6', 6) arranged along a continuous extent of the extensible material all of which are separable from the attached portion 2. This allows the formation of a larger initial loop of the extensible material. FIG. 3 is a further variation of this concept where three separable ends 7 are provided creating five (5) separable bridging portions (6, 6', 6, 6', 6) arranged along a continuous extent of the extensible material forming the disposal tape 1.

Figure 4:
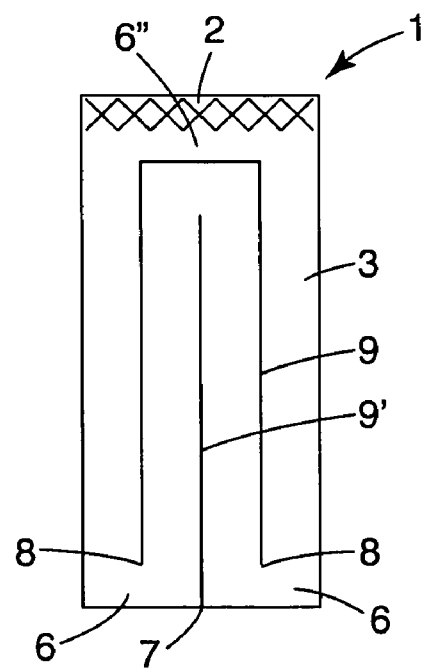
FIG. 4 is a plan view of another embodiment of an expandable disposal tape of the present invention.

A line of separation 9' with a separable end 7 can also result in two or more discrete loops. This occurs where the opposite terminal end 8'(of a line of separation 9 with a separable end 7) does not create a separable bridging portion 6', but rather a bridging portion 6 that is associated with a side edge of the disposal tape, preferably a side edge that includes the attached portion 2. This is shown, for example in FIG. 4. In FIG. 4 the line of separation 9' has a separable end 7 and an opposite terminal end 8", which creates a bridging portion 6" that is associated with the side edge of the disposal tape 1 associated with the attached portion 2. This bridging portion 6" remains attached to the article allowing the formation of two loops.

A line of separation can be formed in any suitable manner. For example a line of separation could be a continuous or discontinuous slit provided in the expandable portion. A cutting blade or a die cutter could create this slit. With discontinuous slits, connected portions could be left that are easily severable, for example perforation cuts. Attached portions or perforation cuts may be desirable for embodiments, such as shown in FIGS. 2-4, having separable ends 7 to prevent these ends from separating and creating flagging issues during manufacturing or use. A line of separation could also be a cut out portion provided in the expandable portion, or created during a deposition process used to form the disposal tape. The terminal ends 8, 8' or 8" of the cut out portions could be provided with a means to reduce tear propagation such as a grommet, weld or reinforcement.

Where the expandable portion is formed from an elastically extensible material, suitable elastic materials would include conventional elastomeric thermoplastic polymers such as polyurethanes, copolyetheresters, polyamide polyether block copolymers, ethylene vinyl acetates (EVA), block copolymers having the general formula A-B-A or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly (styrene/ethylene-butylene/styrene) and the like.

These conventional elastomeric materials could be formed into elastomeric web materials such as elastomeric films, elastomeric fibrous webs such as nonwoven elastic webs or laminates. If nonelastomeric webs or layers are laminated to elastomeric webs the webs can be joined by any conventional mean such as adhesives, thermobonding, ultrasonic welding, or extrusion lamination. The elastic web can be extended when joined to the nonelastic web or if not extended subjected to a stretch activation step. Coextruded films can also be formed with inelastic layers, such as described in U.S. Pat. No. 5,773,374, the substance of which is incorporated by reference in its entirety. If an elastic material is laminated or joined to an inelastic web or layer, this may require that the laminate be made elastic prior to use but if easily extensible the laminate could be used as is, where by user stretching the inelastic layer is permanently deformed allowing the elastic material to elastically recover. The laminate could also be made elastic by the manufacturer, such as by stretching an elastic laminate with an attached inelastic web, attaching an inelastic web to a stretched elastic web, attaching an elastic web to a corrugated inelastic web, or attaching an elastic web to a necked inelastic web.

Where the expandable portion is a plastically deformable portion, suitable deformable plastic materials would include any web material or laminate that in general could extend to the desired degree of extension at a relatively low force (at room temperature), such as less than 5.0 kg/25 m and preferably less that 3.0 kg/25 mm. Suitable extensible webs could be films, nonwovens or laminates of these materials formed from conventional polymers such as polyolefins like polypropylene, polyethylene and copolymers (block, random or random block or the like) and blends with other inelastic or elastic olefins or nonolefinic resins such as polyester, polyamides, urethanes or the like.

As shown in FIG. 2b the disposal tape 1 could be provided with a printed graphical image or otherwise formed to allow it to be differentiated from the disposable article to which it is attached. This could be by any suitable image, such as a pattern, a picture, or the like. Alternatively, the disposal tape could be colored or textured to stand out from the disposable article to which it is attached.

Figure 1B:
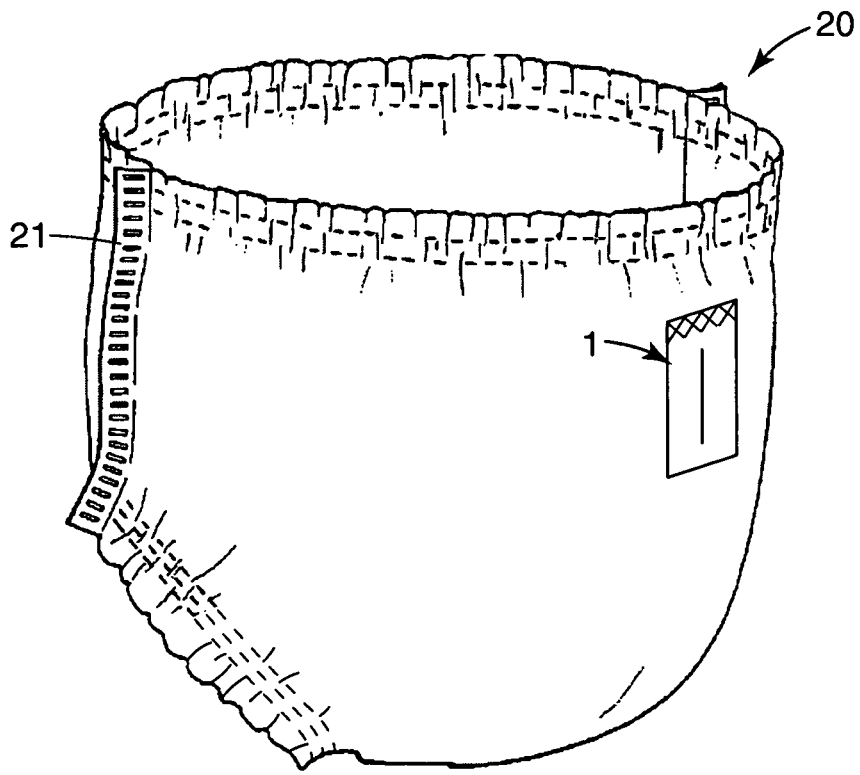
Figure 5:
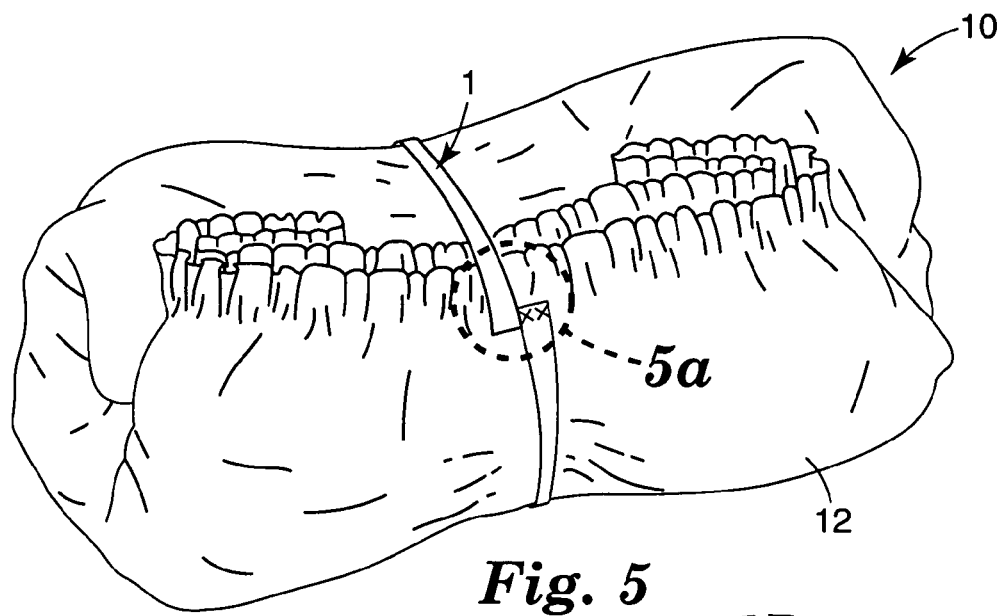
FIG. 5 is a perspective view of a disposable diaper rolled up for disposal using the expandable disposal tape of the present invention.
Figure 5A:
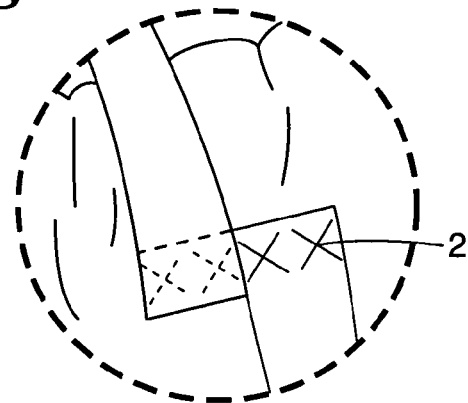
FIG. 5a is an exploded view of the disposed tape of FIG. 5.

In use, the disposal tape would be opened or expanded to form a loop, which loop would be then appropriately extended by extending the extensible web material and wrapping the extended loop around the folded or rolled up disposable article as shown in FIGS. 5 and 5a, which shows the disposal tape of FIG. 1a in use. FIG. 1b shows this identical disposal tape on an alternative disposable article 20, namely a pull-on type diaper, which has breakable side seams 21. This pull on diaper would be disposed of in substantially the identical manner as the diaper shown in FIG. 5.

Figure 6:
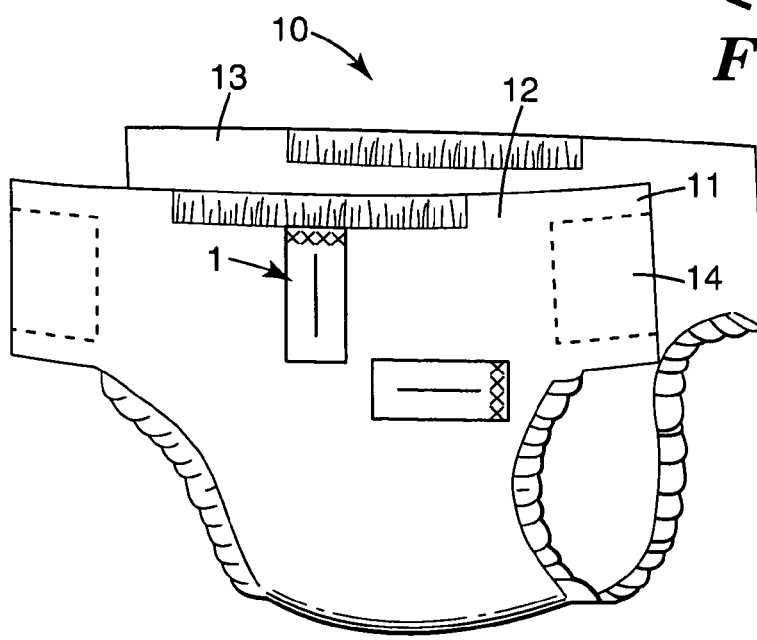
FIG. 6 is a perspective view of a disposable diaper using two expandable disposal tapes of the present invention.
Figure 7:
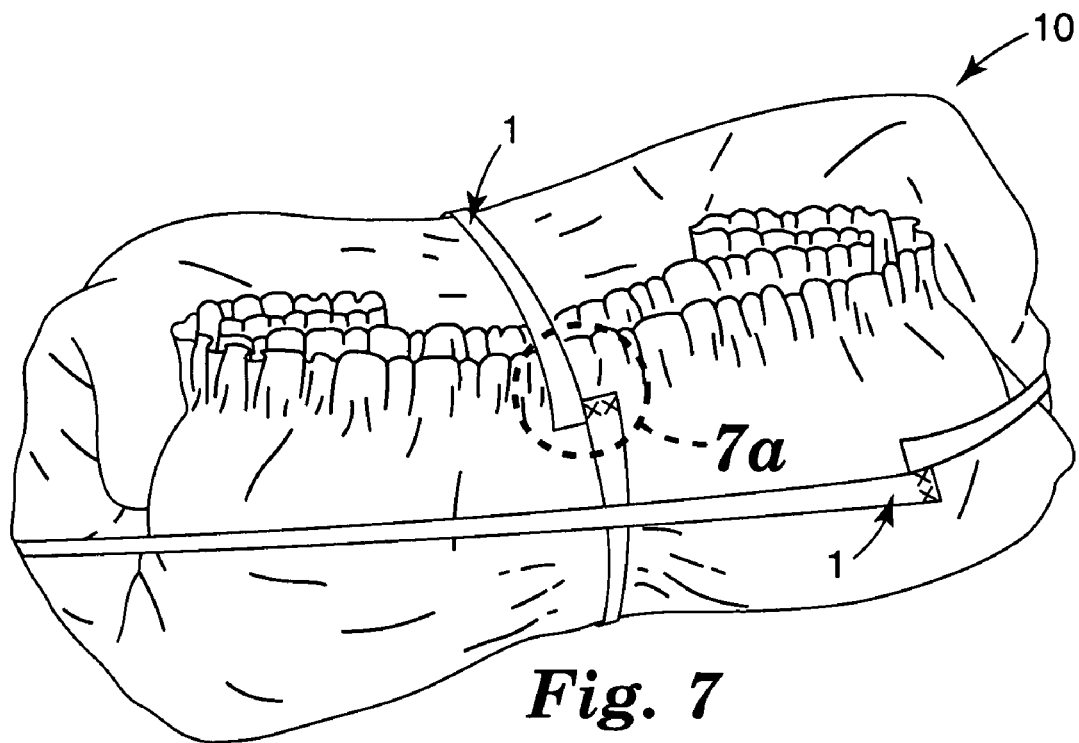
FIG. 7 is a perspective view of a disposable diaper of FIG. 6 in a rolled form using the two expandable disposal tapes of the present invention.
Figure 7A:
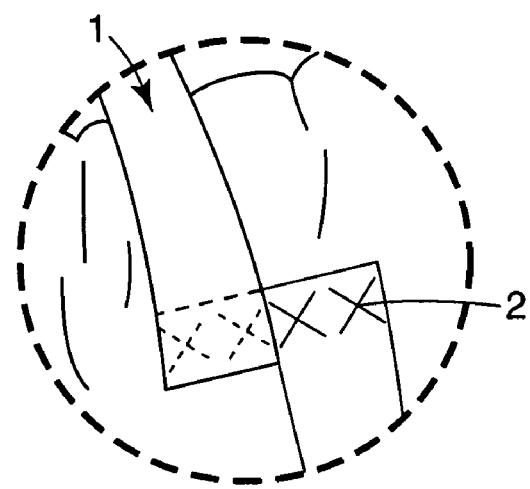
FIG. 7a is an exploded view of the disposal tape of FIG. 7.

FIG. 6 shows using two disposal tapes 1, such as shown in FIGS. 1a and 1b, used on a disposable diaper as shown in FIG. 1a, which could be used as shown in FIGS. 7 and 7a. FIG. 7 is the diaper of FIG. 6 in rolled form with the two expandable disposal tapes 1 expanded and wrapped around the diaper in different directions. FIG. 7a is an exploded view of the expandable disposal tape 1 on the diaper similar to FIG. 5a.

Figure 8:
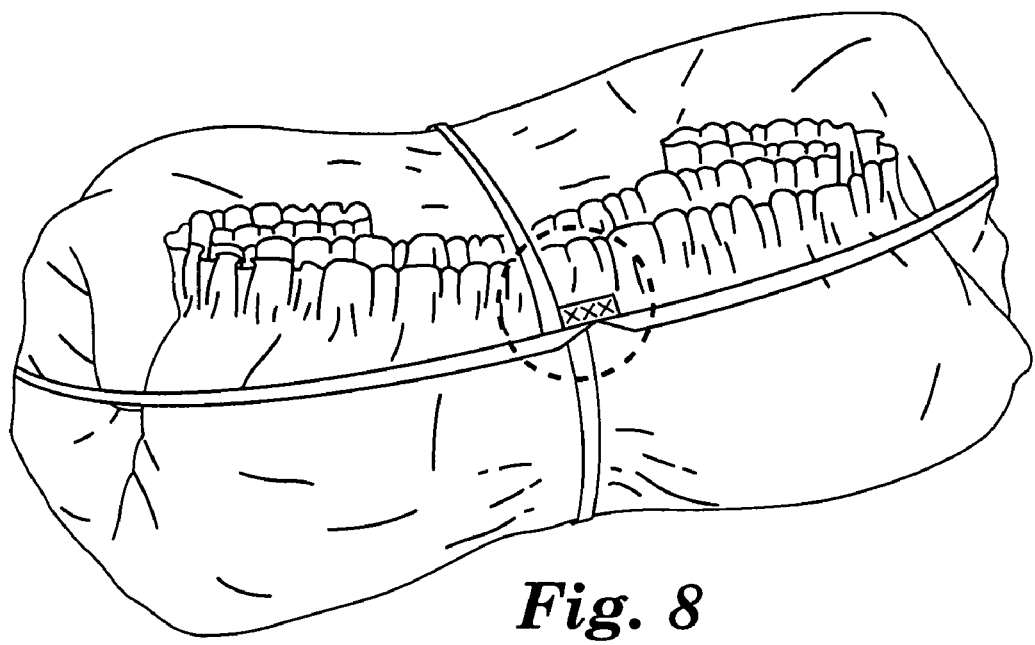
FIG. 8 is a perspective view of a disposable diaper in a rolled form using the expandable disposal tape of FIG. 4.
Figure 8A:
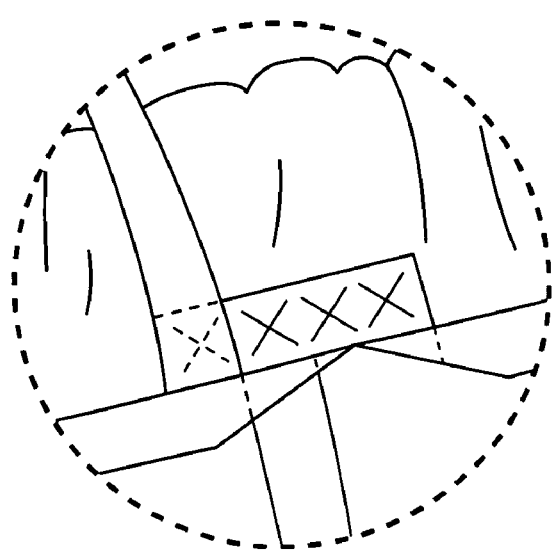
FIG. 8a is an exploded view of the disposal tape of FIG. 8.

FIG. 8 shows the expandable disposal tape 41 of FIG. 4 used on a diaper, as in FIG. 7, where two loops are formed extended by the user in two directions. FIG. 8a is an exploded view of the expandable disposal tape 41 on the diaper.

The invention claimed is:

1. An expandable disposal tape for use in a disposable absorbent article comprising an extensible base layer, the base layer having an attachable portion and an expandable portion, wherein at least the expandable portion is formed of an extensible web material and further is provided with one or more lines of separation terminating prior to reaching an edge of the expandable portion to form two bridging portions to allow the expandable portion to be expanded to form at least one loop, which loop can be extended by extending the extensible web material.

2. The expandable disposal tape of claim 1 wherein the expandable portion has a length dimension and a width dimension where at least one line of separation extends along the length and/or width to provide at least two terminal ends for the at least one line of separation forming the two bridging portions.

3. The expandable disposal tape of claim 2 wherein there is at least one second line of separation starting at a side edge of the expandable portion or another line of separation, which line of separation forms a separable end and a terminal end which terminates prior to an opposing side edge of the expandable portion, or another line of separation forming a bridging portion.

4. The expandable disposal tape of claim 3 wherein the second line of separation terminates prior to another line of separation forming a separable bridging portion.

5. The expandable disposal tape of claim 3 wherein the second line of separation terminates prior to the attachable portion forming a bridging portion with two adjacent lines of separation, provided with two terminal ends, forming two extensible loops.

6. The expandable disposal tape of claim 1 wherein the bridging portion has a width of from 1 mm to 50 mm.

7. The expandable disposal tape of claim 6 wherein the bridging portion has a width of from 2 to 30 mm.

8. The expandable disposal tape of claim 2 wherein the line of separation is substantially parallel to at least one side edge of the expandable portion.

9. The expandable tape of claim 2 wherein the line of separation is a slit provided in the expandable portion.

10. The expandable tape of claim 2 wherein the line of separation is a cut out portion provided in the expandable portion.

11. The expandable tape of claim 2 wherein the extensible web material is an elastically extensible web.

12. The expandable disposal tape of claim 2 wherein the extensible web material is a plastically extensible web.

13. The expandable disposal tape of claim 2 wherein the attachable portion is provided with an adhesive layer.

14. The expandable disposal tape of claim 2 wherein the attachable portion is provided with an adhesive layer and a reinforcement layer.

15. The expandable disposal tape of claim 11 wherein the attachable portion is less extensible than the extensible web material forming the expandable portion.

16. The expandable disposal tape of claim 9 wherein the elastically extensible web is formed of an elastic film.

17. The expandable disposal tape of claim 14 wherein the elastically extensible web is an elastic film laminate including a nonwoven layer.

18. The expandable disposal tape of claim 1 wherein the expandable disposal tape has a printed graphic image.

19. A disposable absorbent article having at least one expandable disposal tape comprising an extensible base layer, the base layer having an attachable portion and an expandable portion, wherein at least the expandable portion is formed of an extensible web material and further is provided with one or more lines of separation terminating prior to reaching an edge of the expandable portion to form two bridging portions to allow the expandable portion to be expanded to form at least one loop, which loop can be extended by extending the extensible web material.

20. The disposable absorbent article of claim 19 wherein the expandable portion has a length dimension and a width dimension where at least one line of separation extends along the length and/or width to provide at least two terminal ends for the at least one line of separation forming the two bridging portions.

21. The disposable absorbent article of claim 20 wherein there is at least one second line of separation starting at a side edge of the expandable portion or another line of separation, which line of separation forms a separable end and a terminal end which terminates prior to an opposing side edge of the expandable portion, or another line of separation forming a bridging portion.

22. The disposable absorbent article of claim 21 wherein the second line of separation terminates prior to another line of separation forming a separable bridging portion.

23. The disposable absorbent article of claim 21 wherein the second line of separation terminates prior to the attachable portion forming a bridging portion with two adjacent lines of separation, provided with two terminal ends, forming two extensible loops.

24. The disposable absorbent article of claim 19 wherein the bridging portion has a width of from 1 mm to 50 mm.

25. The disposable absorbent article of claim 24 wherein the bridging portion has a width of from 2 to 30 mm.

26. The disposable absorbent article of claim 20 wherein the line of separation is substantially parallel to at least one side edge of the expandable portion.

27. The disposable absorbent article of claim 20 wherein there are two or more disposal tapes provided on the disposable absorbent article.

28. The disposable absorbent article of claim 20 wherein the attachable portion permanently bonded to the disposable article.

29. The disposable absorbent article of claim 28 wherein the attachable portion is joined to the disposable absorbent article with an adhesive.

30. The disposable absorbent article of claim 19 wherein the expandable disposal tape is removably attached to the disposable absorbent article.

\* \* \* \* \*